(12) United States Patent
Krivoruchko et al.

(10) Patent No.: US 7,318,837 B2
(45) Date of Patent: Jan. 15, 2008

(54) CUSTOMIZED ALLOYS FOR STENTS

(75) Inventors: Michael Krivoruchko, Forestville, CA (US); Joseph Lessar, Coon Rapids, MN (US); Richard Francis, White Bear Lake, MN (US); Matthew Birdsall, Santa Rosa, CA (US); Darrel Untereker, Oak Grove, MN (US); Jeffrey Allen, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 30 days.

(21) Appl. No.: 11/278,052

(22) Filed: Mar. 30, 2006

(65) Prior Publication Data

US 2007/0233231 A1 Oct. 4, 2007

(51) Int. Cl.
*A61F 2/06* (2006.01)

(52) U.S. Cl. ...................... 623/1.15; 424/426
(58) Field of Classification Search ....... 623/1.15–1.48
See application file for complete search history.

(56) References Cited

U.S. PATENT DOCUMENTS

| 4,733,665 | A | 3/1988 | Palmaz |
| 4,800,882 | A | 1/1989 | Gianturco |
| 4,886,062 | A | 12/1989 | Wiktor |
| 5,133,732 | A | 7/1992 | Wiktor |
| 5,292,331 | A | 3/1994 | Boneau |
| 5,421,955 | A | 6/1995 | Lau et al. |
| 5,776,161 | A | 7/1998 | Globerman |
| 5,935,162 | A | 8/1999 | Dang |
| 6,090,127 | A | 7/2000 | Globerman |
| 6,113,627 | A | 9/2000 | Jang |
| 6,168,571 | B1 | 1/2001 | Solar et al. |
| 6,527,802 | B1 | 3/2003 | Mayer |
| 6,663,661 | B2 | 12/2003 | Boneau |
| 6,730,116 | B1 | 5/2004 | Wolinsky et al. |
| 6,855,161 | B2 | 2/2005 | Boylan et al. |
| 6,899,730 | B1 | 5/2005 | Rivelli, Jr. |
| 6,904,310 | B2 | 6/2005 | Knapp et al. |
| 6,911,100 | B1 | 6/2005 | Gibbs et al. |
| 6,929,660 | B1 | 8/2005 | Ainsworth et al. |
| 6,945,993 | B2 | 9/2005 | Kveen et al. |
| 2001/0044651 | A1 | 11/2001 | Steinke et al. |
| 2005/0096734 | A1 | 5/2005 | Majercak et al. |
| 2006/0276875 | A1* | 12/2006 | Stinson et al. ............. 623/1.15 |
| 2007/0038291 | A1* | 2/2007 | Case et al. ................ 623/1.16 |
| 2007/0132156 | A1* | 6/2007 | Burgermeister et al. .... 264/479 |

FOREIGN PATENT DOCUMENTS

| EP | 0804934 | 11/1997 |
| WO | WO00/07522 | 2/2000 |

\* cited by examiner

*Primary Examiner*—Suzette Gherbi

(57) ABSTRACT

A balloon-expandable stent formed from a customized alloy formulation. The stent alloy has a either a high, variable or no work hardening rate, very high modulus of elasticity (Young's modulus), and a low yield point. A stent constructed of a material with this combination of properties undergoes significant plastic deformation upon deployment in vivo to its implantation diameter and exhibits minimum recoil for better sizing. The plastic deformation also raises the subsequent yield point of the stent material resulting in a stronger stent upon implantation that is more resistant to vascular loading.

8 Claims, 4 Drawing Sheets

CUSTOMIZED ALLOYS FOR STENTS

FIELD OF THE INVENTION

The present invention relates to endoluminal prostheses, and more particularly to stents, constructed from metallic alloys that exhibit a high modulus of elasticity, a low yield point, and a high work hardening rate, a variable work hardening rate, or exhibit no work hardening.

BACKGROUND OF THE INVENTION

A wide range of medical treatments exist that utilize "endoluminal prostheses." As used herein, endoluminal prostheses is intended to cover medical devices that are adapted for temporary or permanent implantation within a body lumen, including both naturally occurring and artificially made lumens, such as without limitation: arteries, whether located within the coronary, mesentery, peripheral, or cerebral vasculature; veins; gastrointestinal tract; biliary tract; urethra; trachea; hepatic shunts; and fallopian tubes.

Accordingly, a wide assortment of endoluminal prostheses have been developed, each providing a uniquely beneficial structure to modify the mechanics of the targeted lumen wall. For example, stent prostheses are known for implantation within body lumens to provide artificial radial support to the wall tissue, which forms the various lumens within the body, and often more specifically, for implantation within the blood vessels of the body.

To provide radial support to a vessel, such as one that has been widened by a percutaneous transluminal coronary angioplasty, commonly referred to as "angioplasty," "PTA" or "PTCA", a stent is implanted in conjunction with the procedure. Effectively, the stent must overcome the natural tendency of the vessel walls of some patients to close back down. As such, the stent acts as a scaffolding to resist the vessels tendency to close back down. Under this procedure, the stent may be collapsed to an insertion diameter and inserted into a body lumen at a site remote from the diseased vessel. The stent may then be delivered to the desired treatment site within the affected lumen and deployed, by self-expansion or radial expansion, to its desired diameter for treatment.

In certain instances due to the stretching of the vessel wall that occurs during a PTCA procedure, the stretching and widening of the vessel to reopen the lumen and the subsequent making of the vessel patent for facilitating revascularization of the heart tissue can result in vessel injury at the treatment site. The resulting trauma to the vessel wall contributes to the extent and occurrence of restenosis of the vessel. A problem associated with stent expansion at the treatment site is that the stent may need to be over expanded in order to compensate for metallurgical recoil, which occurs in high strength stents. This over expansion can contribute to the trauma that occurs to the vessel wall.

Accordingly, a vascular stent must possess a unique set of properties so that it can travel through small and tortuous body lumens to the treatment site, as well as be expanded to no more than its working diameter to provide consummate lumen expansion and radial support subsequent to implantation. Ideally, the stent should be formed from a material that exhibits a very high modulus of elasticity, a very low yield point, a high tensile strength, a variable work hardening rate, and good fatigue resistance, and that provides flexibility to the stent for navigating the tortuous vascular anatomy. Further, a radially-expandable stent must undergo significant plastic deformation when being expanded into its deployed state, which requires a stent material to have good elongation or ductility. Finally, an ideal stent material should have a high degree of radiopacity, good corrosion resistance and biocompatibility to vascular tissue, blood and other bodily fluids. However, these requirements are often competing and/or contradictory, such that a sacrifice or trade-off between one or more properties is customarily required in choosing a stent material.

Stents are typically constructed from metal alloys that include any of stainless steel, nickel-titanium (NiTi or nitinol), cobalt-chromium (MP35N), platinum, and other suitable metals. Customarily such commercially available materials are designed for one or two properties, e.g., strength and endurance, at the sacrifice of others, e.g., formidability and/or processability. Therefore, a need exists in the art for a stent made from a customized material that possesses the right balance of mechanical properties for making the vascular stent with optimal properties.

BRIEF SUMMARY OF THE INVENTION

The present invention is directed to a stent constructed of a customized alloy. In one embodiment, a balloon-expandable stent is formed from an alloy having a high work hardening rate, a high modulus of elasticity and a low yield point. Upon implantation, a stent constructed of such a material undergoes significant plastic deformation with minimum recoil. The stent material may contain at least 30% iridium, with a strain hardening exponent in the range of 0.1-0.3 and a modulus of elasticity is in the range of between 207 GPa to 243 GPa.

In another embodiment, a balloon-expandable stent is made from an alloy having a moderate modulus of elasticity, and a low yield point and exhibits no work hardening. Upon implantation, a stent constructed of such a material undergoes significant plastic deformation with minimum recoil. The alloy may consist of at least one element selected from a group consisting essentially of tantalum, niobium, stainless steel, and cobalt based alloys and have a modulus of elasticity is in the range of between 207 GPa to 243 GPa.

In another embodiment, a balloon-expandable stent is made from an alloy having a variable work hardening rate, a high modulus of elasticity and a low yield point. Upon implantation, a stent constructed of such a material undergoes significant plastic deformation with minimum recoil. The alloy may have a variable strain hardening exponent in the range of 0.5-0.6 at low strains of 1% to 5% that varies to between 0.1-0.3 at higher strains of 5% to 10%.

DETAILED DESCRIPTION OF THE INVENTION

Figure 1:
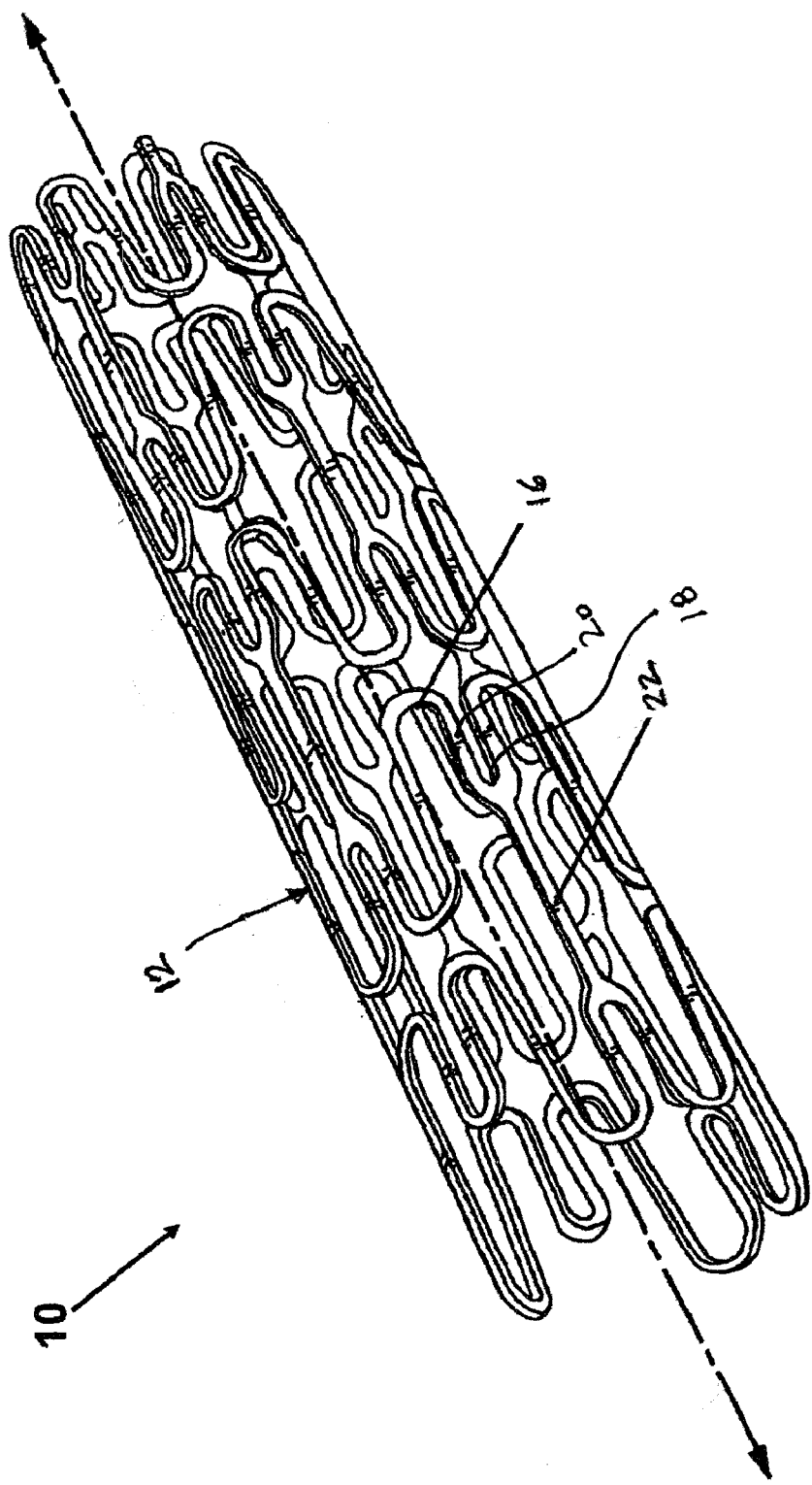
FIG. 1 is a perspective view of an exemplary stent in accordance with an embodiment of the present invention.

Embodiments according to the present invention are directed to a balloon-expandable stent made from a customized alloy. FIG. 1 illustrates an exemplary stent 10 in accordance with an embodiment of the present invention. Stent 10 is a patterned tubular device that includes a plurality of radially expandable cylindrical rings 12. Cylindrical rings 12 are formed from struts 14 formed in a generally sinusoidal pattern including peaks 16, valleys 18, and generally straight segments 20 connecting peaks 16 and valleys 18. Connecting links 22 connect adjacent cylindrical rings 12 together. In FIG. 1, connecting links 22 are shown as generally straight links connecting a peak 16 of one ring 12 to a valley 18 of an adjacent ring 12. However, connecting links 22 may connect a peak 16 of one ring 12 to a peak 16 of an adjacent ring, or a valley to a valley, or a straight segment to a straight segment. Further, connecting links 22 may be curved. Connecting links 22 may also be excluded, with a peak 16 of one ring 12 being directly attached to a valley 18 of an adjacent ring 12, such as by welding, soldering, or the manner in which stent 10 is formed, such as by etching the pattern from a flat sheet or a tube. It will be appreciated by those ordinary skill in the art that stent 10 of FIG. 1 is merely an exemplary stent and that stents of various forms and methods of fabrication can be used in accordance with various embodiments of the present invention. For example, in a typical method of making a stent, a thin-walled, small diameter metallic tube is cut to produce the desired stent pattern, using methods such as laser cutting or chemical etching. The cut stent may then be de-scaled, polished, cleaned and rinsed. Some examples of methods of forming stents and structures for stents are shown in U.S. Pat. No. 4,733,665 to Palmaz, U.S. Pat. No. 4,800,882 to Gianturco, U.S. Pat. No. 4,886,062 to Wiktor, U.S. Pat. No. 5,133,732 to Wiktor, U.S. Pat. No. 5,292,331 to Boneau, U.S. Pat. No. 5,421,955 to Lau, U.S. Pat. No. 5,935,162 to Dang, U.S. Pat. No. 6,090,127 to Globerman, and U.S. Pat. No. 6,730,116 to Wolinsky et al., each of which is incorporated by reference herein in its entirety.

The customized alloy also may be used in any of the balloon-expandable stent designs disclosed in U.S. Pat. No. 5,776,161, U.S. Pat. No. 6,113,627, and U.S. Pat. No. 6,663,661, which are incorporated by reference herein in their entirety.

Figure 2:
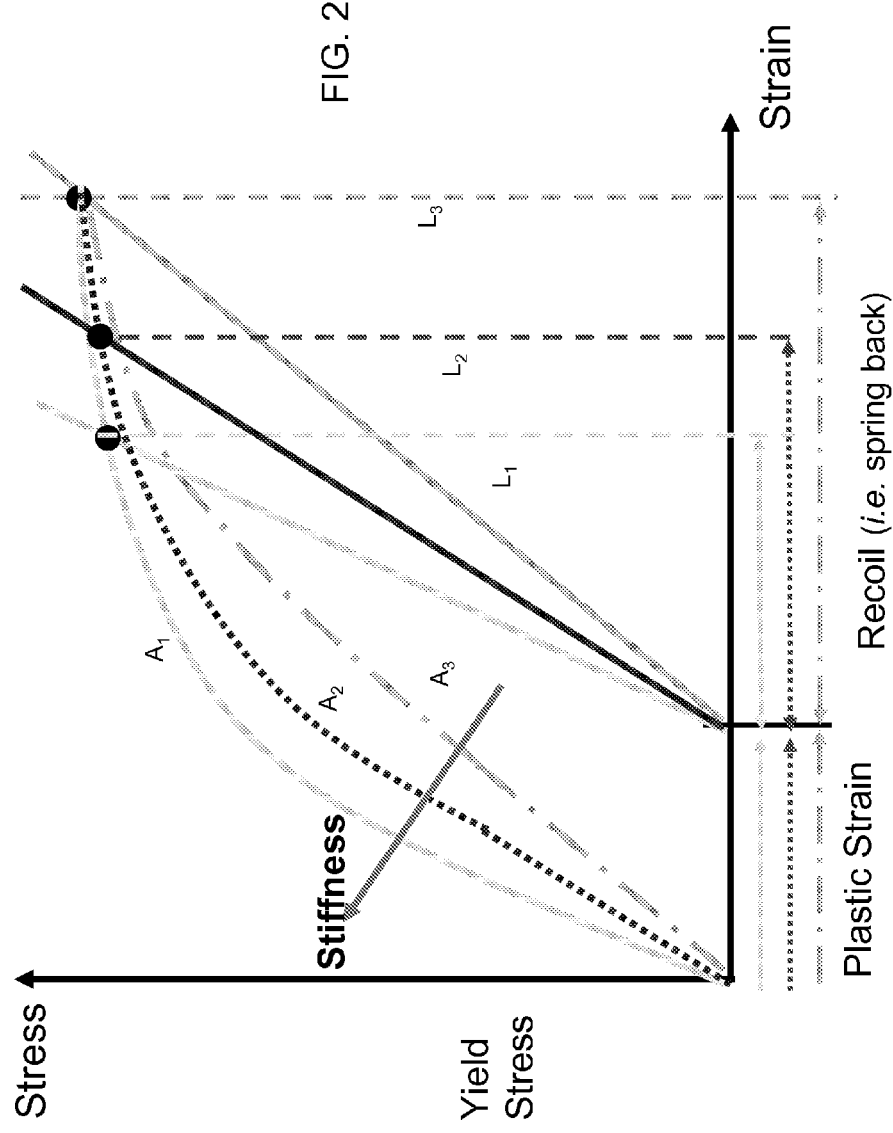
FIG. 2 is a graph showing the stress-strain curve of a stent material having a high modulus of elasticity and a high work hardening rate according to an embodiment of the present invention.

FIG. 2 shows stress-strain curves $A_1$, $A_2$, and $A_3$ of a stent material according to an embodiment of the present invention. The alloy depicted by curve $A_1$ has a very high modulus of elasticity, an example of such an alloy would be iridium, or molybdenum, whereas the alloy depicted by curve $A_2$ has a mid-range modulus of elasticity, an example of such an alloy would be tantalum, 316SS, or MP35N, and the alloy depicted by curve $A_3$ has a lower modulus of elasticity, an example of such an alloy would be tin or magnesium. The modulus of elasticity, E, i.e., Young's modulus, is a material constant and is an index of the stiffness of the material. The higher the value of E the stiffer the material. Accordingly, curve $A_1$ represents the alloy with the highest modulus of elasticity. In one embodiment, the modulus of elasticity, E, is greater than 207 GPa. In another embodiment, E is in the range of 207 GPa to 243 GPa. In another embodiment, E is in the range of 516 GPa to 528 GPa.

The alloy represented by curve $A_1$ also has a high work hardening rate, i.e., $d\sigma/d\epsilon$. The alloy represented by curve $A_2$ has a moderate work hardening rate. The alloy represented by curve $A_3$ has a low work hardening rate. Work hardening effects can be measured by a value called the "strain hardening exponent," where $\sigma = \kappa \epsilon^n$ and "n" is the strain hardening exponent and K is the strength coefficient. The strain-hardening exponent may have values from n=0 (perfectly plastic solid) to n=1 (elastic solid). For most metals, "n" has values between 0.10 and 0.50. A value for "n" for a high work hardening rate alloy according to the present invention is in the range of 0.1 to 0.3. It is important to note that the rate of strain hardening is not identical with the strain-hardening exponent. The larger the value of "n" the higher the work hardening rate. In another embodiment the present invention, a material which has a variable strain hardening exponent is to be selected. In one embodiment, a material according to the present invention has a strain hardening exponent in the range of 0.5-0.6 at low strains of 1% to 5% that then changes to be in the range of 0.1-0.3 at higher strains of 5% to 10%.

Resilience is the capacity of a material to absorb energy when it is deformed elastically and then, upon unloading to have this energy recovered. For the alloys depicted by curves $A_1$, $A_2$, and $A_3$, the resiliency of the material is represented by the area of the elastic region of the graphs. The elastic region of each graph is the area under the respective curve $A_1$, $A_2$, and $A_3$ to lines $L_1$, $L_2$, and $L_3$, respectively. $L_1$, $L_2$, and $L_3$ extend from the yield point of the respective alloy to the x-axis. This region is found to be equivalent to the modulus of resilience $U_R = (\text{yield stress})^2 / 2E$, where E is Young's modulus for the material. Modulus of resilience is a measure of the energy input required or work needed to be done to cause plastic deformation to a nominal unit volume of material, in essence it provides a metric for the inherent "springiness" of the material. With reference to FIG. 2, a stent constructed from the high work hardening alloy depicted by curve $A_1$, the least resilient alloy, would exhibit less recoil upon implantation, whereas a stent constructed from the low work hardening alloy depicted by curve $A_3$, the most resilient alloy, would exhibit more recoil upon implantation.

An embodiment according to the present invention includes an alloy that has an exceptionally high work hardening rate, very high modulus of elasticity (Young's modulus), and a low yield point, as represented by curve $A_1$ in FIG. 2. In accordance with this embodiment, a low yield point is yielding of the material in a stress range of 30-80 ksi. Such an alloy may be achieved by adding up to 30% iridium to platinum. Platinum has good formability and radiopacity, but has a low work hardening rate and tensile strength. Iridium in its pure form (i.e., not as part of an alloy) is generally not considered a good material for vascular devices, such as stents, because it is relatively brittle (not ductile) with poor elongation in its polycrystalline form. Despite its drawbacks, iridium has characteristics that are beneficial in vascular devices, such as excellent corrosion resistance, high strength, high modulus of elasticity, a rapid work-hardening rate, and excellent biocompatibility. By using up to 30% iridium, an alloy is created that has significantly increased strength and work hardening, as well as good radiopacity and formability that make it a useful material for a medical device application. In another embodiment, a commercially available Co—Cr alloy, e.g., MP35N or L605, may be modified to achieve the desired properties of a good work hardening rate, high modulus of elasticity, a low yield point and radiopacity by substituting one of its constituents, e.g., molybdenum, nickel, with a high atomic number element, such as platinum, iridium or tungsten.

A stent constructed with the properties of the high work hardening rate alloy of FIG. 2, undergoes significant plastic deformation upon deployment in vivo to an implantation diameter, e.g., 3.0 mm, 3.5 mm, etc. The plastic deformation raises the subsequent yield point of the stent material resulting in a stronger stent upon implantation. Thus, a stent constructed from a customized alloy with a variable work hardening rate according to the present invention is more resistant to vascular loading.

Figure 3:
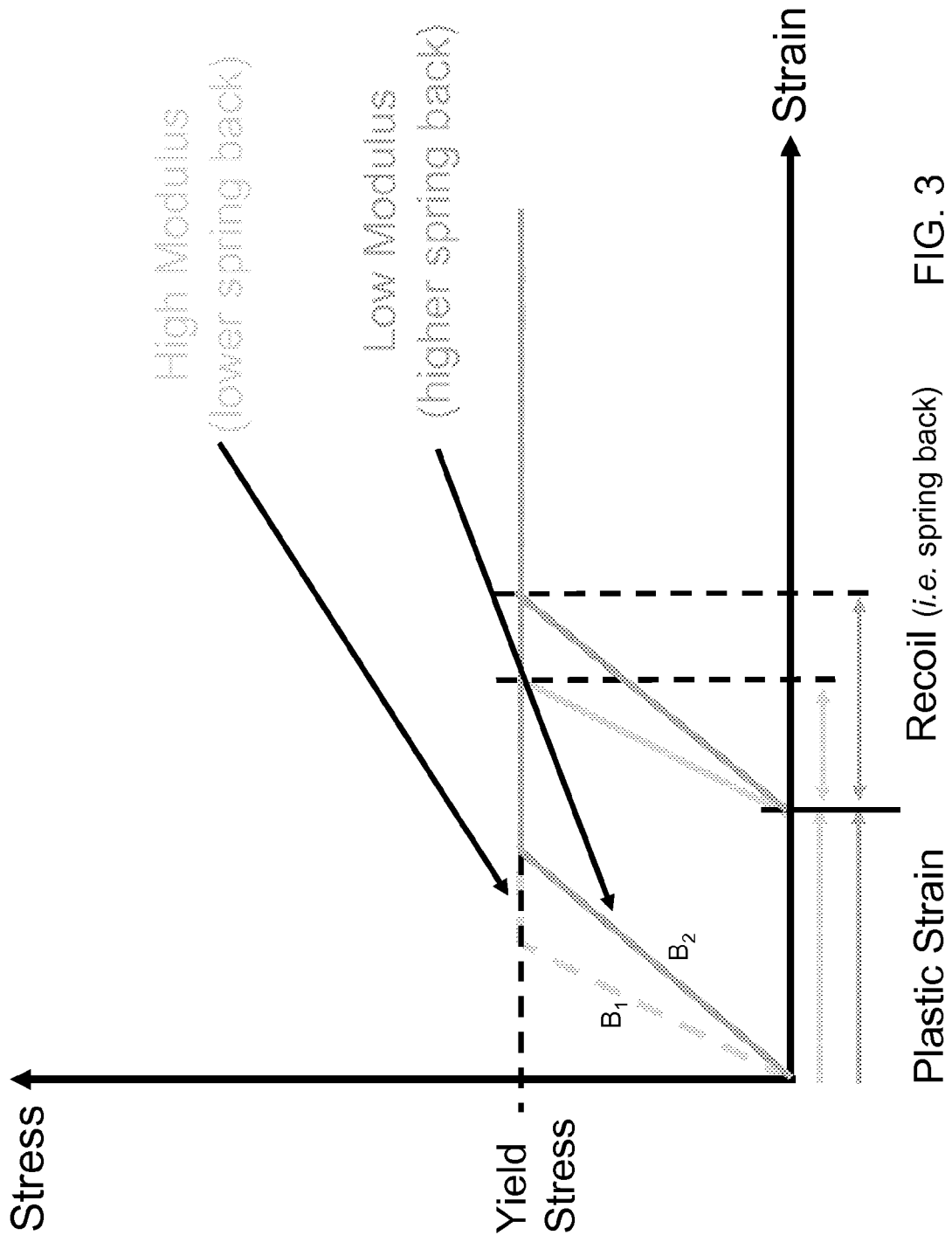
FIG. 3 is a graph showing the stress-strain curve of a stent material that has a high modulus of elasticity but undergoes low or zero work hardening according to an embodiment of the present invention.

Another embodiment of the present invention includes an alloy that has a very high modulus of elasticity (Young's modulus), a low yield point and virtually no work hardening, as represented by curve $B_1$ in FIG. 3. During expansion of a stent constructed with the properties of the alloy of FIG. 3, the stent still undergoes a significant amount of plastic deformation, but the material of the stent does not work harden. The stent has minimal recoil and, therefore, is more accurately sized upon implantation Thus, over-expansion of the stent is minimized, as less force is require to plastically deform the stent to its working diameter, thereby reducing trauma to the vessel wall during placement.

Curve $B_2$ in FIG. 3 depicts a material with a lower modulus of elasticity and a low yield point that exhibits no work hardening during plastic deformation. Due to the lower modulus of elasticity, a stent constructed of this material would be less stiff and have greater spring back making it less desirable than the inventive stent alloy depicted by curve $B_1$.

Figure 4:
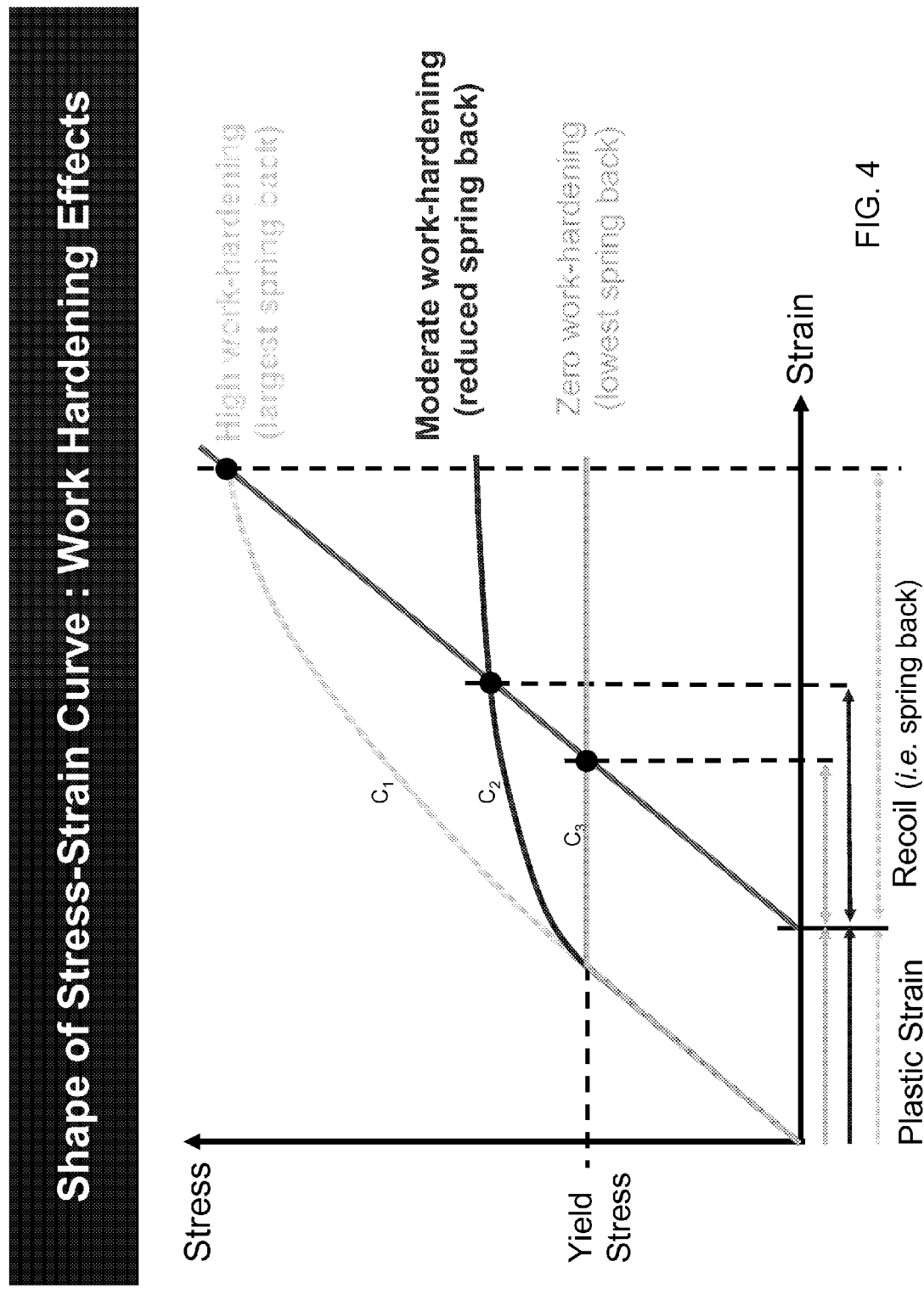
FIG. 4 is a graph showing the stress-strain curve of various stent materials, each having the same modulus of elasticity but with varying work hardening rates, according to an embodiment of the present invention.

FIG. 4 shows stress-strain curves $C_1$, $C_2$, and $C_3$ of a stent material according to another embodiment of the present invention. Each of the alloys has essentially the same modulus of elasticity, as is evident by the overlapping of each of the linear portions of the respective stress-strain curves $C_1$, $C_2$, and $C_3$. Each of these materials has a moderate modulus of elasticity in the range of 135 Gpa to 275 Gpa and a low yield point. In accordance with this embodiment, a low yield point is yielding of the material in a stress range of 30-80 ksi. The alloy depicted by curve $C_1$ has a high work hardening rate and the alloy depicted by curve $C_2$ has a mid-range work hardening rate, whereas the alloy depicted by curve $C_3$ undergoes no work hardening. In this embodiment, a stent made from the non-work hardened alloy depicted by curve $C_3$ requires minimal pressure to size during deployment, which aids to minimize the propensity for over-expansion of the stent and causing added trauma to the vessel. The stent also will exhibit less recoil than a stent constructed of a material that exhibits a stress-strain curve similar to curves $C_1$ and $C_2$. In a further embodiment, such an alloy according to this embodiment of the present invention includes tantalum, niobium, stainless steel, and cobalt based alloys, which have moderate modulus of elasticity, low yield points and low work hardening rates. In another embodiment, the same alloy, for example, a Co—Cr or precipitation hardenable stainless steel 17-4 PH, may be used but the percentage of elemental constituents may be varied or the alloy may receive various heat treatments to exhibit the stress-strain curves depicted by $C_1$, $C_2$, and $C_3$.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

The invention claimed is:

1. A balloon-expandable stent comprising:
a stent comprised of an alloy having a high work hardening rate with a strain hardening exponent in the range of 0.1-0.3, a high modulus of elasticity and a low yield point, wherein upon implantation the stent undergoes significant plastic deformation with less than 10% recoil.

2. The stent of claim 1, wherein the alloy further comprises iridium.

3. The stent of claim 2, wherein the alloy contains at least 30% iridium.

4. The stent of claim 1, wherein the modulus of elasticity is in the range of between 207 GPa to 243 GPa.

5. The stent of claim 1, wherein the modulus of elasticity is in the range of between 516 GPa to 528 GPa.

6. A balloon-expandable stent comprising:
a stent comprised of an alloy having a moderate modulus of elasticity in the range of between 207 GPa to 243 GPa, a low yield point and no work hardening, wherein upon implantation the stent undergoes significant plastic deformation with less than 10% recoil.

7. The stent of claim 6, wherein the alloy further consists of at least one element selected from a group consisting essentially of tantalum, niobium, stainless steel, and cobalt based alloys.

8. A balloon-expandable stent comprising:
a stent comprised of an alloy having a variable work hardening rate with a variable strain hardening exponent in the range of 0.5-0.6 at low strains of 1% to 5% that varies to between 0.1-0.3 at higher strains of 5% to 10%, a high modulus of elasticity and a low yield point, wherein upon implantation the stent undergoes significant plastic deformation with less than 10% recoil.

* * * * *